United States Patent
Kondow et al.

(10) Patent No.: US 7,223,568 B2
(45) Date of Patent: May 29, 2007

(54) METHODS FOR DETERMINING NUCLEOTIDE SEQUENCES OF SINGLE NUCLEIC ACID MOLECULES

(75) Inventors: Tamotsu Kondow, Tokyo (JP); Fumitaka Mafune, Tokyo (JP); Yoshihiro Takeda, Chiba (JP)

(73) Assignees: Toyota Jidosha Kabushiki Kaisha, Toyota-shi (JP); Genesis Research Institute, Incorporated, Nagoya-shi (JP)

( * ) Notice: Subject to any disclaimer, the term of this patent is extended or adjusted under 35 U.S.C. 154(b) by 46 days.

(21) Appl. No.: 09/996,591

(22) Filed: Nov. 30, 2001

(65) Prior Publication Data

US 2002/0143167 A1 Oct. 3, 2002

Related U.S. Application Data

(63) Continuation of application No. PCT/JP01/02806, filed on Mar. 30, 2001.

(30) Foreign Application Priority Data

Mar. 30, 2000 (JP) .......................... 2000-94727

(51) Int. Cl.
| | |
|---|---|
| *C12P 19/34* | (2006.01) |
| *C12Q 1/68* | (2006.01) |
| *C07H 21/02* | (2006.01) |
| *C07H 21/04* | (2006.01) |
| *C07H 21/00* | (2006.01) |

(52) U.S. Cl. .................... 435/91.2; 435/6; 435/91.1; 536/23.1; 536/24.3; 536/24.33; 536/25.3; 536/25.32

(58) Field of Classification Search ............ 435/6, 435/91.1, 91.2, 183; 436/94; 536/23.1, 24.3, 536/24.33, 25.3, 25.32

See application file for complete search history.

(56) References Cited

U.S. PATENT DOCUMENTS

| | | | |
|---|---|---|---|
| 4,729,947 A | 3/1988 | Middendorf et al. | |
| 5,075,216 A | 12/1991 | Innis et al. | 435/6 |
| 5,091,652 A * | 2/1992 | Mathies et al. | 250/458.1 |
| 5,112,736 A * | 5/1992 | Caldwell et al. | 435/6 |
| 5,302,509 A * | 4/1994 | Cheeseman | 435/6 |
| 5,547,839 A | 8/1996 | Dower et al. | |
| 5,942,422 A * | 8/1999 | Rothstein | 435/91.1 |
| 6,136,543 A * | 10/2000 | Anazawa et al. | 435/6 |
| 6,613,513 B1 * | 9/2003 | Parce et al. | 435/6 |

FOREIGN PATENT DOCUMENTS

| | | |
|---|---|---|
| EP | 0 969 083 A1 | 1/2000 |
| WO | WO 90/13666 | 11/1990 |
| WO | WO 91/06678 | 5/1991 |
| WO | WO 93/05183 | 3/1993 |
| WO | WO 93/213340 | 10/1993 |
| WO | WO 94/23064 | 10/1994 |
| WO | WO 98/58240 | 12/1998 |
| WO | WO 00/06770 | 2/2000 |

OTHER PUBLICATIONS

Yoshihiro Takeda, et al., "Kyou Shouten Laser Keikou Kenbikyou ni yoru Youekichuu no Tanitsu Shikiso Bunshi no Kenshutsu", vol. 49, No. 1 (Feb., 2000) pp. 17–18; With 5-page English translation.

Yoshihiro Takeda, et al., "Kyou Shouten Laser Keikou Kenbikyou ni yoru Youekichuu no Tanitsu Shikiso Bunshi no Kenshutsu", Bunko Kenkyu, vol. 49, No. 1 (Feb. 2000) pp. 17–18; With 5-page English translation.

* cited by examiner

*Primary Examiner*—Ethan Whisenant
*Assistant Examiner*—Frank Wei Min Lu
(74) *Attorney, Agent, or Firm*—Oblon, Spivak, McClelland, Maier & Neustadt, P.C.

(57) ABSTRACT

The present invention relates to a method for determining a nucleotide sequence of a nucleic acid by detecting a single dye molecule.

22 Claims, 2 Drawing Sheets

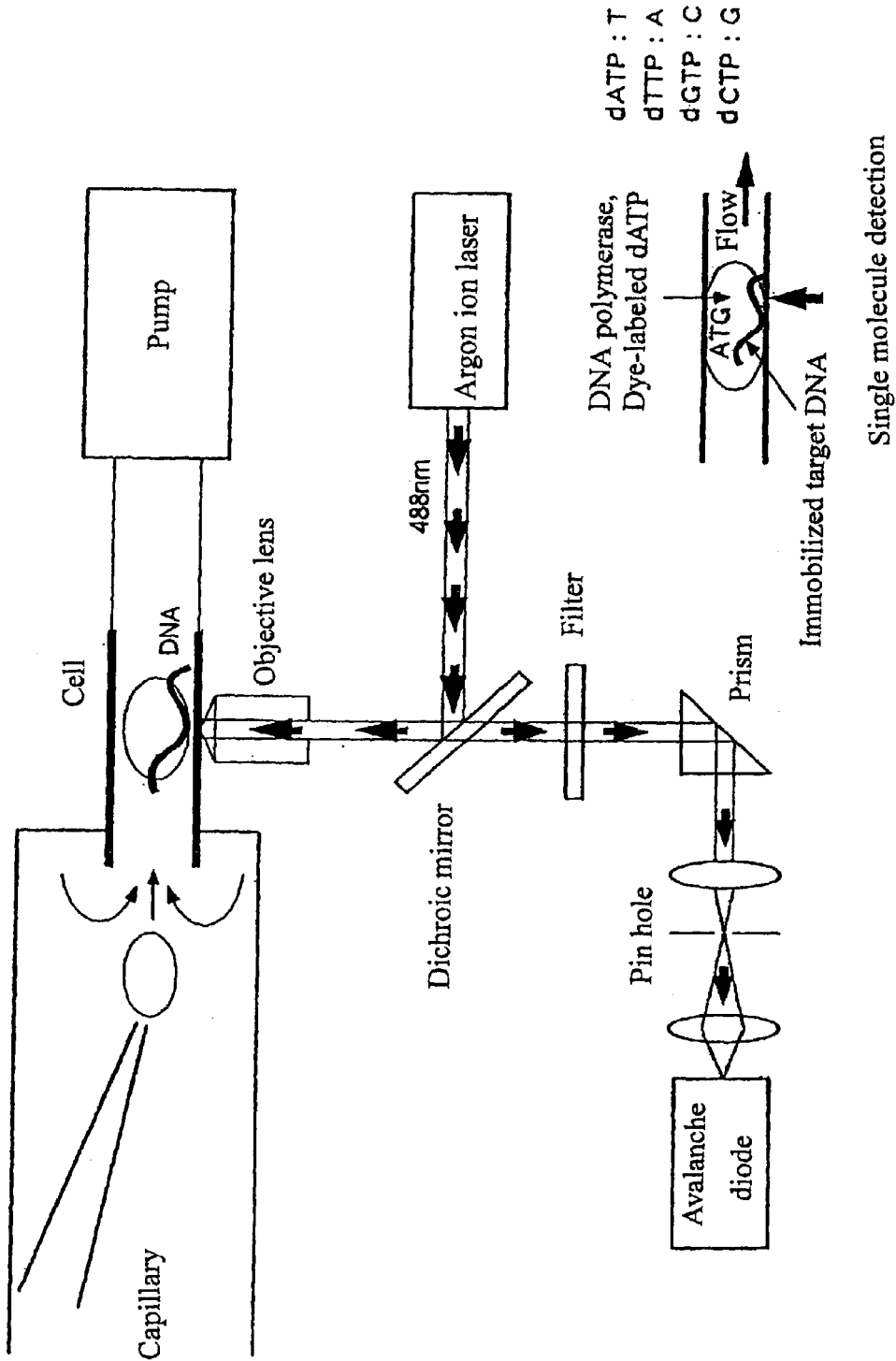

METHODS FOR DETERMINING NUCLEOTIDE SEQUENCES OF SINGLE NUCLEIC ACID MOLECULES

BACKGROUND OF THE INVENTION

1. Field of the Invention

The present invention relates to a method for determining nucleotide sequences of single nucleic acid molecules by single molecule detection.

2. Description of the Background

The Sanger method (Proc. Natl. Acad. Sci. USA, 74:5463, 1977) is routinely used as a method for determining a nucleotide sequence of DNA. This method is also referred to as the dideoxy chain termination method, entailing the steps of annealing a primer to the 5' end of a DNA sample, synthesizing a complementary chain in the presence of DNA polymerase and four deoxynucleoside triphosphates (dNTPs where N denotes A, C, T and G) and each of 2', 3'-dideoxynucleoside triphosphates (ddNTPs where N denotes A, C, T or G), stopping the elongation reaction at a position where ddNTP is incorporated, and performing gel electrophoresis for the obtained reaction product, thereby determining a nucleotide sequence of the DNA sample. The DNA fragments formed at this time are generally labeled with a radioactive label, which enables the identification of the position of the fragments.

Furthermore, since radioactive labeling requires a special facility, other methods for determining nucleotide sequences which employ fluorescent labels in place of radioactive labels to detect fluorescence by irradiation of a laser beam, have also been developed (e.g. Japanese Patent No. 2901004, and JP-B-7-43347).

However, the use of the Sanger method remains problematic as, for example it requires production of a large number of copies of the DNA to be sequenced by previously incorporating the DNA into a vector, e.g. M13, and that the number of detectable bases is limited to a maximum 1,000 bp per lane of electrophoresis. Hence, if the nucleotide sequence of a DNA could be determined by directly identifying the bases from the 5' end of the sequence one by one, and an isolated single DNA molecule could be used for direct sequencing without requiring a number of replicated molecules of DNA, efficiency of sequencing could, thereby, be significantly improved.

SUMMARY OF THE INVENTION

Accordingly, it is the object of the present invention to provide a method for determining nucleotide sequences of single nucleic acid molecules by single molecule detection. This method advantageous by enables detection of nucleic acid bases one by one, in addition to enabling direct decoding of intracellular DNA or RNA molecules. Furthermore, the present method thereby improves the speed of sequencing by one to two orders of magnitude and enables direct sequencing without producing a number of copies of a single-stranded nucleic acid molecule.

It is, thus, an object of the present invention to provide, in one aspect, a method for determining a nucleotide sequence of a nucleic acid molecule by single dye molecule detection, which entails the steps of:

(a) immobilizing a nucleic acid molecule onto the surface of a solid;
(b) annealing a primer, which has a sequence complementary to a part of the sequence of the nucleic acid molecule, to the nucleic acid molecule;
(c) providing a solution which contains DNA polymerase and one type of dye-labeled dNTP (where N is A, T or U, G or C), or RNA polymerase and one type of dye-labeled NTP (where N is A, U, G or C), to the immobilized nucleic acid molecule, and allowing the nucleotide to react with the 3' end of the primer, whereby a nucleotide, which forms a base-pair with a base opposed to the reaction site, is bound to the primer by action of the polymerase;
(d) detecting a bound, dye-labeled dNTP or NTP;
(e) disrupting the dye molecule of the bound, dye-labeled dNTP or NTP;
(f) repeating the steps (3) to (5) while changing the type of the dye-labeled dNTP or NTP in turn, to sequentially bind dNTPs or NTPs complementary to the nucleotides of the nucleic acid molecule; and
(g) determining a nucleotide sequence of the nucleic acid molecule based on the types of the sequentially bound dNTPs or NTPs.

Moreover, it is another aspect, the present invention to provide a method for determining a nucleotide sequence of a nucleic acid by single dye molecule detection, which entails the steps of:

(a) immobilizing onto the surface of a solid, a primer which has a sequence complementary to a part of the sequence of a nucleic acid molecule to be measured;
(b) annealing the nucleic acid molecule to the primer;
(c) providing a solution, which contains DNA polymerase and one type of dye-labeled dNTP (where N is A, T or U, G or C), or RNA polymerase and one type of dye-labeled NTP (where N is A, U, G or C), to the immobilized nucleic acid molecule, and allowing the nucleotide to react with the 3' end of the primer, whereby a nucleotide, which forms a base-pair with a base opposed to the reaction site, is bound to the primer by action of the polymerase;
(d) detecting a bound, dye-labeled dNTP or NTP;
(e) disrupting the dye molecule of the bound, dye-labeled dNTP or NTP;
(f) repeating the steps (3) to (5) while changing the type of the dye-labeled dNTP or NTP in turn, to sequentially bind dNTPs or NTPs complementary to the nucleotides of the nucleic acid molecule; and
(g) determining a nucleotide sequence of the nucleic acid molecule based on the types of the sequentially bound dNTPs or NTPs.

In one embodiment of the present invention, the solid surface in the above step (1) is the inner wall of a capillary.

In another embodiment of the present invention, the above step (4) comprises optically detecting the dye molecule of the dye-labeled dNTP or NTP. More specifically, the detection can be performed by exciting the dye molecule by irradiation of a laser beam and detecting the thus emitted fluorescence signal. An example of such a detection method is a method, which employs a confocal fluorescence microscope system.

In yet another embodiment of the present invention, the disruption of dye molecules in the above step (5) is performed by irradiation of a laser beam stronger than that in step (4).

In still another embodiment of the present invention, the above dye is a fluorescent dye.

In a further another embodiment of the present invention, the above solution consists of a droplet, in which an aqueous solution containing the dye-labeled dNTP or NTP, is entrapped within a hydrophobic liquid.

BRIEF DESCRIPTION OF THE DRAWINGS

FIG. 2 is a schematic diagram showing the procedure to detect a fluorescent signal derived from a dye molecule using a confocal fluorescence microscope system.

DETAILED DESCRIPTION OF THE PREFERRED EMBODIMENTS

Figure 1:
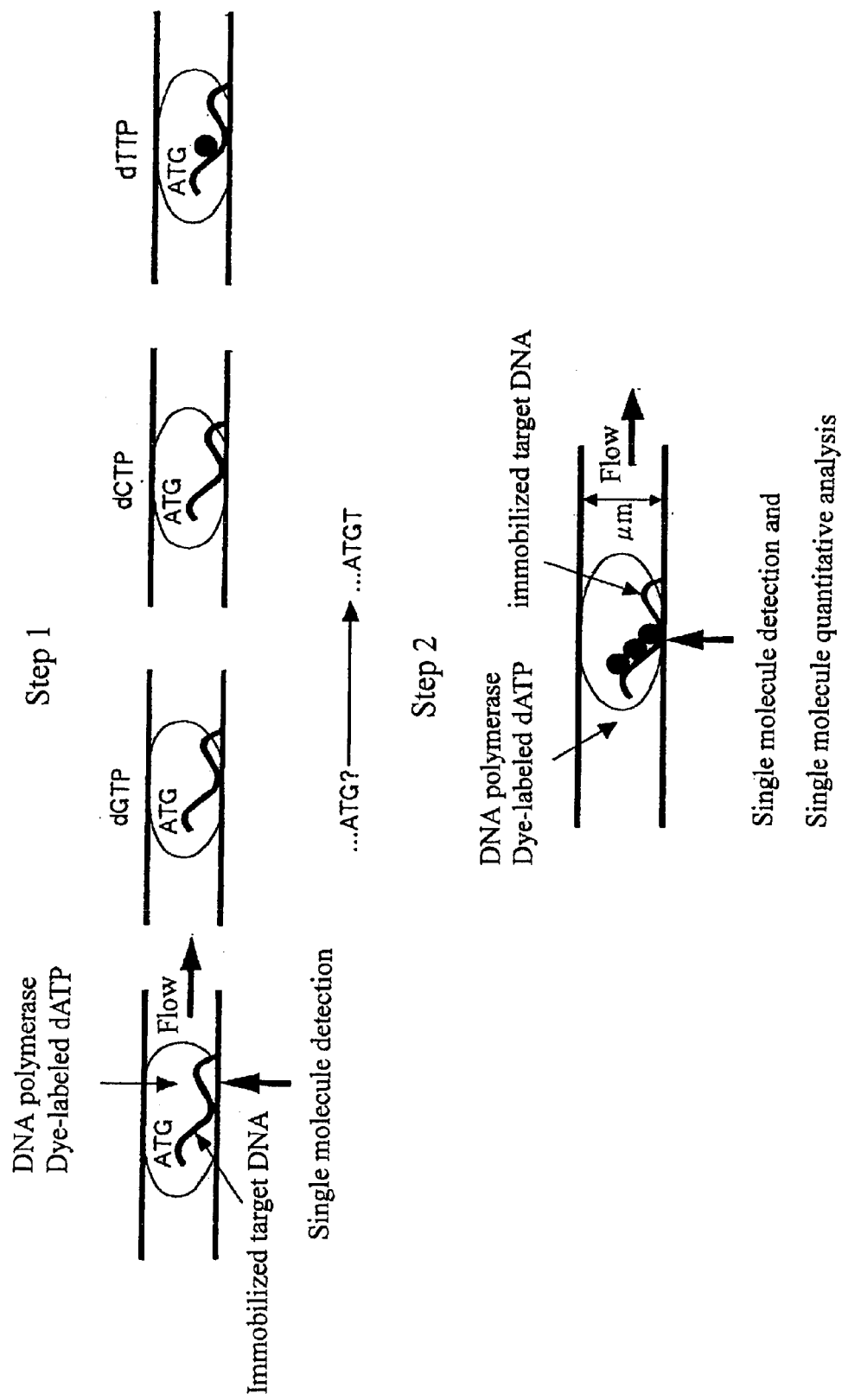
FIG. 1 is a schematic diagram showing the method of the present invention for determining a nucleotide sequence of DNA by single dye molecule detection.

The present invention provides a method for determining nucleotide sequences of nucleic acid molecules comprising DNA or RNA by using a single molecule detection method. The single molecule detection method as used herein means a method, in which any signal molecule is detected by any analysis method. In this invention, generally the dye molecule of a dye-labeled deoxynucleoside triphosphate (dNTP, wherein N denotes A, T or U, G or C) or a dye-labeled nucleoside triphosphate (NTP, wherein N denotes A, U, G or C) can be optically detected using a spectroscopic instrument. The detection is performed by using a confocal fluorescence microscope instrument in the Example described below (see FIG. 2).

The present invention will be now be further described as follows by referring to FIG. 1.

The first step in the method of the present invention entails immobilizing a nucleic acid molecule or a primer having a sequence complementary to a part of the sequence of the nucleic acid molecule, onto the surface of a solid.

The nucleic acid molecule can be immobilized onto the solid surface after purification of a nucleic acid sample by standard techniques, for example by preparing single-stranded molecules from the sample by, for example, denaturation with alkaline treatment.

The size and type of the primers employed are not specifically limited as long as they can be annealed to nucleic acid molecules. For example, the size of the primers may be at least 10 nucleotides, and normally about 15 to 30 nucleotides. When a part of the sequence of a nucleic acid molecule to be sequenced is known, a primer may be prepared based on this known sequence and be used. Alternately, random primers or oligo dT primers may be used as the primers.

The solid surface used may be of any material as long as a nucleic acid molecule or a primer can be immobilized thereto. Examples of such a material include glass, quartz and resin. Further, the solid surface may be flat, curved or in any other form. For example, the inner wall of a capillary (e.g. made of glass, quartz or resin) can be used as a solid surface. A capillary is appropriate for automatically injecting a solution containing dye-labeled dNTP or NTP and polymerase enzyme into the inside of the capillary after immobilization of nucleic acid molecules or primers within the capillary. The internal diameter of a capillary is, for example, approximately 100 to 250 µm, and the sufficient length is generally about 10 to 50 mm, but the internal diameter and length are not limited thereto.

Preferably, the solid surface is previously treated so as to facilitate immobilization of a nucleic acid molecule to be sequenced or a primer, and so as not to allow unreacting dye-labeled dNTP or NTP molecules to adsorb to the surface. Binding of a nucleic acid molecule or a primer to the solid surface can be performed by, for example, a general UV crosslinking method. More specifically, a solution prepared by dissolving a nucleic acid in a Carnoy's solution (methanol/acetic acid (3:1 v/v)) is introduced into a quartz glass capillary, then dried and solidified at room temperature. Next, 2×SSC (NaCl 1.75 g, sodium citrate 0.882 g/100 ml) is introduced into the capillary, followed by UV irradiation, thereby binding the nucleic acid to the solid surface. It is preferable to immobilize one molecule of nucleic acid onto the solid surface, but in practice, multiple nucleic acid molecules are immobilized onto the surface. In an actual measurement, diluted nucleic acid molecules (approximately 0.1 to 100 pmol/µl, preferably 30 to 70 pmol/µl) are immobilized onto the solid surface, one immobilized nucleic acid molecule enters into the field of vision, and then sequencing is performed.

The second step entails annealing a primer to the nucleic acid molecule on the solid surface, or annealing the nucleic acid molecule to a primer on the solid surface.

The third step entails providing a solution containing DNA polymerase and one type of dye-labeled dNTP (where N is A, T or U, G or C) or containing RNA polymerase and one type of dye-labeled NTP (where N is A, U, G or C) to the immobilized nucleic acid molecule, and allowing a nucleotide to react with the 3' end of the above primer. At this time, a nucleotide, which forms a base-pair with a base opposed to the reaction site, is bound to the primer by action of the polymerase.

As used herein, the term "one type of" means a certain one of four types of dye-labeled dNTP or NTP. As the result that this "one type" is specified, the type of dNTP or NTP to be actually bound to a primer would be known.

In FIG. 1, a solvent is allowed to flow through a capillary cell in which a nucleic acid molecule has been immobilized, and a solution containing DNA polymerase and only one type of dye-labeled base DATP is introduced into the flow, in order to cause the reaction of the base next to a DNA sequence ATG previously annealed to a target DNA. If no incorporation reaction of the base by DNA polymerase occurs, no dye is detected on the DNA by the single molecule detection because unreacting bases are washed away. In this case, the same procedure is performed for a solution containing another type of base (dGTP, dCTP or dTTP). This procedure is repeated until a base is incorporated into the above DNA sequence and a dye is detected on the DNA. As shown in the figure, which nucleotide follows ATG (in this case, T follows ATG) will be known by allowing a solution containing a dye-labeled dTTP to contact with the target DNA which has been annealed to a primer with ATG already bound to the 3' end, and then detecting the dye. For a DNA sample having the same sequential bases, multiple bases may be incorporated into a DNA sequence. In such a case, identification of the number of dyes by, for example, fluorescence intensity, enables detection of the number of sequential bases incorporated.

In the present invention, a solution containing DNA polymerase and one type of dye-labeled dNTP (where N is A, T or U, G or C), or RNA polymerase and one type of dye-labeled NTP (where N is A, U, G or C), can consist of a droplet in which an aqueous solution which contains the dye-labeled dNTP or NTP is entrapped within a hydrophobic liquid such as mineral oil. Such a droplet can be easily prepared using, for example, a micro-injector. The size of a droplet is, for example, approximately 10 to 25 µm in diameter, corresponding to several hundreds fL in volume.

Examples of a solvent to flow through a capillary cell are those in which dye-labeled dNTP or NTP and polymerase can be dissolved, including a buffer containing, for example, 67 mM KPO4 (pH7.5), 6.7 mM MgCl2, and 1 mM 2-mercaptoethanol. When a droplet is used, a preferred solvent is one that has no affinity with the droplet. For example, light white oil (d=0.84 g/ml; general commercial name: mineral oil) can be used.

Examples of dyes for labeling dNTP or NTP include fluorophors or luminophors, such as rhodamine and fluorescein (e.g. teteramethyl rhodamine, TMR, emission wavelength: 570 nm; tetramethyl rhodamine isothiocyanate, TRITC, emission wavelength: 573 nm; Rhodamine 6 G, emission wavelength: 550 nm; fluorescein isothiocyanate, FITC, emission wavelength: 515 nm). In addition, 4-fluoro- 7-nitro-benzofurazon (NBD-F, emission wavelength: 540 nm), Texas red (emission wavelength: 605 nm) or the like can be used. In the method of this invention, the same dye may be used regardless of the type of bases, that is dNTP or NTP, or the dye may differ according to the type of bases. To simplify the procedure, dNTP or NTP is preferably labeled with the same dye. In binding a dye to dNTP or NTP, a commercially available product (i.e., dye-labeled dNTP or NTP) may be used, or otherwise, such a product may be synthesized according to a method described in literature (e.g. J. Histochem. Cytochem. 44(5):525–529, 1996).

The fourth step entails detecting a bound, dye-labeled dNTP or NTP.

As shown in FIG. 2, a bound, dye-labeled dNTP or NTP is detected by irradiation of a laser beam to the nucleic acid molecule using, for example, a confocal fluorescence microscope system, and introducing fluorescent signals emitted from the excited dye molecule into a detector to count the number of photons and thereby detect the fluorescent signals.

In FIG. 2, the excitation light (488 nm) of an argon ion laser is reflected by a dichroic mirror to focus on a DNA sample through an objective lens, a fluorescent signal emitted from the dye molecules excited by the excitation light is introduced into a confocal pin hole (e.g. 50 μm in diameter) through a band pass filter, and then the number of photons that have reached a detector (e.g. avalanche photodiode) is counted by a multichannel counter, thereby detecting the fluorescent signal. The presence of a band pass filter enables to selectively take fluorescent signals. Further the presence of a pin hole eliminates unnecessary light.

The fifth step entails disrupting dye molecules of bound, dye-labeled dNTP or NTP.

The method of the present invention requires disruption of dye molecules, after a dye molecule is detected after reaction of dye-labeled dNTP or NTP on a nucleic acid molecule, but before the next dye-labeled dNTP or NTP is bound. As a means for this purpose, for example a method of irradiation of a laser beam, which is stronger than that in step (4) (e.g., about 10 mW) can be used.

The sixth step entails sequentially binding a dNTP or NTP, which forms a base-pair with the nucleotide of the nucleic acid molecule, by repeating the above steps (3) to (5) while changing the type of dye-labeled dNTP or NTP in turn.

As used herein, the word "changing the type of dye-labeled dNTP or NTP in turn" means to keep changing the type of base introduced until binding occurs. That is, if no binding occurs when a certain base of the four types of dye-labeled dNTP or NTP is delivered at a nucleic acid molecule, then another certain base is delivered. If no binding occurs again, then yet another certain base is delivered at the nucleic acid molecule. Whether or not binding of bases occurs is confirmed by step (4), and the dye molecule of a bound base is disrupted in step (5). The procedures from steps (3) to (5) are repeated sequentially up to the (maximum) number of bases of the nucleic acid molecule.

The seventh step entails determining a nucleotide sequence of the nucleic acid molecule based on the types of the sequentially bound dNTPs or NTPs.

EXAMPLES

The present invention will be now described in more detail by reference to certain Examples which are provided solely for illustration and are not intended to be limitative.

Example 1

A Capton-coated quartz glass capillary (200 μm in internal diameter×20 mm in length; purchased from GL Science, Japan) was heated with a burner, thereby burning and removing a portion of the Capton coating to provide an observation window for a microscope. The capillary was immersed in 1M KOH, and then in a conc. H2SO4/30%H2O2 (1:2 v/v) mixture, thereby eliminating oil or organic matter attached on the glass surface and washing. Next, a template DNA was immobilized onto the inner wall of the glass capillary by the UV crosslinking method. That is, a solution prepared by dissolving DNA in a Carnoy's solution (methanol/acetic acid (3:1 v/v)) was introduced into the inside of the glass capillary, then dried and solidified at room temperature. Subsequently, 2×SSC (NaCl 1.75 g and sodium citrate 0.882 g/100 ml) was introduced into the capillary, followed by irradiation with UV, thereby binding DNA to the solid surface. Here, the concentration of the template DNA in the Carnoy's solution was 50 pmol/μl, so that DNA could be immobilized at a density sparse enough to confirm the reaction on a single template DNA.

Next, DNA polymerase reaction was performed for the template DNA. The reaction solution was prepared by dissolving a primer having a sequence complementary to the template DNA, DNA polymerase (Klenow Fragment, purchased from TOYOBO) and a dye-labeled nucleotide in a buffer solution (67 mM KPO4, pH7.5, 6.7 mM MgCl2, 1 mM 2-mercaptoethanol). The reaction solution was allowed to react with the template DNA, performing an incorporation reaction.

After reaction, the reaction solution was removed, and then the same solvent as described above was allowed to flow through the capillary for washing. Then, the inner wall of the glass capillary was observed for a bound dye using a confocal fluorescence microscope system. That is, the dye molecule of a dye-labeled nucleotide was excited by a laser beam, and the resulting fluorescence was observed. At this time, the template DNA was previously immobilized on the inner wall surface of the glass capillary at a density sparse enough to allow confirmation of an incorporation reaction on a single template DNA.

More detailed description of experimental examples will be given, as follows.

Reagents Used

```
    Template DNA No. 1                                            (SEQ ID NO: 1)
5'-CTG CTC ATA TAT ATA TAG GTG CCA GTC GGA TAG TGT T-3'

Template DNA No. 2                                            (SEQ ID NO: 2)
5'-GCG GAG GAA GGT CCT TGG TCA TTA GGA TCC-3'

Primer No. 1                                                  (SEQ ID NO: 3)
5'-AAC ACT ATC CGA CTG GCA CC-3'

Primer No. 2                                                  (SEQ ID NO: 4)
5'-GGA TCC TAA TGA CCA AGG-3'
```

Dye-labeled Nucleotides

BODYPY-TMR-dUTP (purchased from FUNAKOSHI; absorbance wavelength 544 nm, fluorescence wavelength 570 nm)

TMR-dATP (purchased from Daiichi Pure Chemicals; absorbance wavelength 550 nm, fluorescence wavelength 570 nm)

TMR-dGTP (purchased from Daiichi Pure Chemicals; absorbance wavelength 550 nm, fluorescence wavelength 570 nm)

Experiment 1 and Results

BODYPY-TMR-dUTP nucleotide was allowed to react with a combination of the template DNA No. 1 and the primer No. 1. In this combination of DNAs, the template DNA has a sequence such that dUTP is incorporated onto the template DNA. The experiment was performed according to the above described method, and as a result, it was confirmed by observing the presence of fluorescence from a single fluorescence molecule that BODYPY-TMR-dUTP nucleotide was incorporated onto the single template DNA. Further, reference test 1 was conducted to confirm that the observed fluorescence was not due to the BODYPY-TMR-dUTP nucleotide non-specifically attached to the inner wall of a glass capillary. That is, the above reaction solution was allowed to react with the surface of a glass capillary containing no template DNA, and as a result, it was confirmed that BODYPY-TMR-dUTP nucleotide was not attached to the glass capillary surface because no fluorescence was observed. Moreover, reference test 2 was conducted using TMR-dATP nucleotide instead of BODYPY-TMR-dUTP nucleotide. In this case, it is predicted that TMR-dATP would not be incorporated into the single template DNA. Actually, it was confirmed that the nucleotide was not incorporated onto the single template DNA because no fluorescence was observed.

Experiment 2 and Results

The same experiment was repeated with the exception that a combination of the template DNA No. 2 and the primer No. 2 was used. In this combination of DNAs, the template DNA has a sequence such that dATP is incorporated onto the template DNA. Comparison of the reaction of TMR-dATP nucleotide to that of TMR-dGTP nucleotide revealed that TMR-dATP was incorporated but TMR-dGTP was not incorporated onto the single template DNA.

Experiment 3 and Results

A laser (10 mW, 488 nm) irradiates, for several seconds, the sample from Experiment 1, in which BODYPY-TMR-dUTP has been incorporated by using a combination of the single template DNA No. 1 and the primer No. 1 on the inner wall of the capillary, thereby disrupting the dye molecule of the dye-labeled nucleotide. Similarly, the sample from Experiment 2, in which TMR-dATP has been incorporated by using a combination of the single template DNA No. 2 and the primer No. 2 on the inner wall of the capillary was treated in the same manner as that described above, so that the dye molecule of the dye-labeled nucleotide was disrupted. For these samples, the reaction of dye-labeled nucleotides was subsequently repeated so that the types of nucleotides incorporated could be specified one after another.

As may readily be appreciated from the above, the present invention enables the decoding of the bases in nucleotide sequences of a nucleic acid, one by one.

The present invention also provides a kit which may be used in practicing the present invention. The kit may generally contain at least i) one or more solutions each containing DNA polymerase and one type of dye-labeled dNTP and/or ii) one or more solutions each containing RNA polymerase and one type of dye-labeled NTP. Optionally, other constituents may be included therein, such as an immobilizing solid surface, such as glass, quartz or resin in any form such as flat, curved or even a capillary, which is preferably pre-treated so as to facilitate immobilization of a nucleic acid thereto.

Further, the kit may generally contain one or a multiplicity of types of dye-labeled dNTP or dye-labeled NTP solutions. The solutions may be an aqueous solution-containing the labeled dyes entrapped in a hydrophobic liquid, such as mineral oil.

Additionally, the kit may be used in conjunction with a laser for irradiation and a confocal fluoresence microscope system for detection, for example, or the kit may include such items.

Sequence Listing Free Text

SEQ ID NO:1—Description of Artificial Sequence: synthesized template DNA

SEQ ID NO:2—Description of Artificial Sequence: synthesized template DNA

SEQ ID NO:3—Description of Artificial Sequence: a primer

SEQ ID NO:4—Description of Artificial Sequence: a primer

What is claimed is:

1. A method for determining a nucleotide sequence of a single nucleic acid molecule, which comprises:
   (a) immobilizing a nucleic acid molecule onto the surface of a solid;
   (b) annealing a primer to said nucleic acid molecule, wherein said primer has a sequence complementary to a part of a sequence of the nucleic acid molecule;
   (c) providing a solution which contains a DNA polymerase and only one type of dye-labeled dNTP, where N is A, T or U, G or C, or an RNA polymerase and only one type of dye-labeled NTP, where N is A, U, G or C, to said immobilized nucleic acid molecule, and allowing the dye-labeled dNTP or NTP to react with the 3' end of said primer, whereby the dye-labeled dNTP or NTP, which forms a base-pair with a base in the nucleic acid molecule at a position where the dye-labeled dNTP or NTP reacts with the 3' end of said primer and is bound to the primer by action of the polymerase;
   (d) detecting a bound, dye-labeled dNTP or NTP;
   (e) disrupting the dye molecule of the bound, dye-labeled dNTP or NTP;
   (f) repeating (c) to (e) while changing the type of dye-labeled dNTP or NTP in turn, to sequentially bind dNTPs or NTPs which forms a base-pair with the nucleotides of the nucleic acid molecule; and
   (g) determining a nucleotide sequence of the nucleic acid molecule based on the types of the sequentially bound dNTPs or NTPs.

2. The method of claim 1, wherein said surface of a solid is the inner wall of a capillary.

3. The method of claim 1, wherein (d) comprises optically detecting the dye molecule of said dye-labeled dNTP or NTP.

4. The method of claim 1, wherein (d) comprises exciting dye molecules by irradiation of a laser beam and detecting a fluorescent signal.

5. The method of claim 1, wherein said detection is performed using a confocal fluorescence microscope system.

6. The method of claim 4, wherein said disrupting the dye molecules in (e) comprises irradiating with a laser beam stronger than the laser beam in (d).

7. The method of claim 1, wherein said dye is a fluorescent dye.

8. The method of claim 1, wherein said dye-labeled dNTP is labeled with rhodamine, tetramethyl rhodamine (fluorescein) Rhodamine 6G, fluorescein isothiocyanate, or 4-fluoro-7-nitro-benzofurazon (Texas Red).

9. The method of claim 1, wherein said dye-labeled NTP is labeled with rhodamine, tetramethyl rhodamine (fluorescein) Rhodamine 6G, fluorescein isothiocyanate, or 4-fluoro-7-nitro-benzofurazon (Texas Red).

10. The method of claim 1, wherein said dNTP or NTP is each labeled with the same dye.

11. The method of claim 1, wherein said solution consists of a droplet in which an aqueous solution containing said dye-labeled dNTP or NTP, is entrapped within a hydrophobic liquid.

12. A method for determining a nucleotide sequence of a single nucleic acid molecule, which comprises:
   (a) immobilizing a primer onto the surface of a solid, wherein the primer comprises a sequence complementary to a part of a sequence in the nucleic acid molecule;
   (b) annealing a nucleic acid molecule to the immobilized primer;
   (c) providing a solution which contains a DNA polymerase and only one type of dye-labeled dNTP, where N is A, T or U, G or C, or an RNA polymerase and only one type of dye-labeled NTP, where N is A, U, G or C, to said immobilized primer, and allowing the dye-labeled dNTP or NTP to react with the 3' end of said primer, whereby the dye-labeled dNTP or NTP, which forms a base-pair with a base in the nucleic acid molecule at a position where the dye-labeled dNTP or NTP reacts with the 3' end of said primer and is bound to the primer by action of the polymerase;
   (d) detecting a bound, dye-labeled dNTP or NTP;

(e) disrupting the dye molecule of the bound, dye-labeled dNTP or NTP;

(f) repeating (c) to (e) while changing the type of dye-labeled dNTP or NTP in turn, to sequentially bind dNTPs or NTPs which forms a base-pair with the nucleotides of the nucleic acid molecule; and (g) determining a nucleotide sequence of the nucleic acid molecule based on the types of the sequentially bound dNTPs or NTPs.

13. The method of claim 12, wherein said surface of a solid is the inner wall of a capillary.

14. The method of claim 12, wherein (d) comprises optically detecting the dye molecule of said dye-labeled dNTP or NTP.

15. The method of claim 12, wherein (d) comprises exciting dye molecules by irradiation of a laser beam and detecting a fluorescent signal.

16. The method of claim 12, wherein said detection is performed using a confocal fluorescence microscope system.

17. The method of claim 15, wherein said disrupting the dye molecules in (e)-comprises irradiating with a laser beam stronger than the laser beam in (d).

18. The method of claim 12, wherein said dye is a fluorescent dye.

19. The method of claim 12, wherein said dye-labeled dNTP is labeled with rhodamine, tetramethyl rhodamine (fluorescein) Rhodamine 6G, fluorescein isothiocyanate, or 4-fluoro-7-nitro-benzofurazon (Texas Red).

20. The method of claim 12, wherein said dye-labeled NTP is labeled with rhodamine, tetramethyl rhodamine (fluorescein) Rhodamine 6G, fluorescein isothiocyanate, or 4-fluoro-7-nitro-benzofurazon (Texas Red).

21. The method of claim 12, wherein said dNTP or NTP is each labeied with the same dye.

22. The method of claim 1, wherein said solution consists of a droplet in which an aqueous solution containing said dye-labeled dNTP or NTP, is entrapped within a hydrophobic liquid.

* * * * *

UNITED STATES PATENT AND TRADEMARK OFFICE
CERTIFICATE OF CORRECTION

PATENT NO. : 7,223,568 B2  
APPLICATION NO. : 09/996591  
DATED : May 29, 2007  
INVENTOR(S) : Yoshihiro Takeda et al.

It is certified that error appears in the above-identified patent and that said Letters Patent is hereby corrected as shown below:

On the Title page Item (75), "Tamotsu Kondow, Tokyo (JP);  
Fumitaka Mafune, Tokyo (JP);  
Yoshihiro Takeda, Chiba (JP)"

should read

--Yoshihiro Takeda, Chiba (JP);  
Fumitaka Mafune, Tokyo (JP);  
Tamotsu Kondow, Tokyo (JP)--

Signed and Sealed this

Twenty-fourth Day of March, 2009

JOHN DOLL  
*Acting Director of the United States Patent and Trademark Office*

UNITED STATES PATENT AND TRADEMARK OFFICE
CERTIFICATE OF CORRECTION

PATENT NO.         : 7,223,568 B2
APPLICATION NO. : 09/996591
DATED                 : May 29, 2007
INVENTOR(S)       : Yoshihiro Takeda et al.

It is certified that error appears in the above-identified patent and that said Letters Patent is hereby corrected as shown below:

Title page Item (57) Under ABSTRACT, "22 Claims" should read --20 Claims--.

Column 9, lines 32 and 33, Claim 1, "(a) immobilizing a nucleic acid molecule onto the surface of a solid;" should read --(a) immobilizing a nucleic acid molecule onto the surface of a solid, wherein the surface of the solid is an inner wall of a capillary;--.

Column 9, line 47, Claim 1, "bound to the primer by action of the polymerase;" should read --bound to the primer by action of the polymerase, wherein the dye-labeled dNTP or NFP is labeled with a dye thereby permitting the incorporation of a sequential dNTP or NTP to the 3' end of the dye-labeled dNTP or NTP and wherein said solution consists of a droplet in which an aqueous solution containing said dye-labeled dNTP or NTP, is entrapped within a hydrophobic solvent and the hydrophobic solvent flows through the capillary;--.

Column 9, line 58, Delete Claim 2 in its entirety.

Column 10, line 52, Claim 12, "tary to a part of a sequence in the nucleic acid molecule;" should read --tary to a part of a sequence in the nucleic acid molecule, wherein the surface of the solid is an inner wall of a capillary;--.

Column 10, line 66, Claim 12, "to the primer by action of the polymerase;" should read --to the primer by action of the polymerase, wherein the dye-labeled dNTP or NTP is labeled with a dye thereby permitting the incorporation of a sequential dNTP or NTP to the 3' end of the dye-labeled dNTP or NTP and wherein said solution consists of a droplet in which an aqueous solution containing said dye-labeled dNTP or NTP, is entrapped within a hydrophobic solvent and the hydrophobic solvent flows through the capillary;--.

UNITED STATES PATENT AND TRADEMARK OFFICE
CERTIFICATE OF CORRECTION

PATENT NO. : 7,223,568 B2
APPLICATION NO. : 09/996591
DATED : May 29, 2007
INVENTOR(S) : Yoshihiro Takeda et al.

It is certified that error appears in the above-identified patent and that said Letters Patent is hereby corrected as shown below:

Column 11, lines 11-12, Delete Claim 13 in its entirety.

Signed and Sealed this

Thirteenth Day of October, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,223,568 B2 | Page 1 of 2 |
| APPLICATION NO. | : 09/996591 | |
| DATED | : May 29, 2007 | |
| INVENTOR(S) | : Yoshihiro Takeda et al. | |

It is certified that error appears in the above-identified patent and that said Letters Patent is hereby corrected as shown below:

Title page Item (57) Under ABSTRACT, "22 Claims" should read --20 Claims--.

Column 9, lines 32 and 33, Claim 1, "(a) immobilizing a nucleic acid molecule onto the surface of a solid;" should read --(a) immobilizing a nucleic acid molecule onto the surface of a solid, wherein the surface of the solid is an inner wall of a capillary;--.

Column 9, line 47, Claim 1, "bound to the primer by action of the polymerase;" should read --bound to the primer by action of the polymerase wherein the dye-labeled dNTP or NTP is labeled with a dye thereby permitting the incorporation of a sequential dNTP or NTP to the 3' end of the dye-labeled dNTP or NTP and wherein said solution consists of a droplet in which an aqueous solution containing said dye-labeled dNTP or NTP, is entrapped within a hydrophobic solvent and the hydrophobic solvent flows through the capillary;--.

Column 9, line 58, Delete Claim 2 in its entirety.

Column 10, line 52, Claim 12, "tary to a part of a sequence in the nucleic acid molecule;" should read --tary to a part of a sequence in the nucleic acid molecule, wherein the surface of the solid is an inner wall of a capillary;--.

This certificate supersedes the Certificate of Correction issued October 13, 2009.

Signed and Sealed this
Eleventh Day of January, 2011

David J. Kappos
*Director of the United States Patent and Trademark Office*

CERTIFICATE OF CORRECTION (continued)
U.S. Pat. No. 7,223,568 B2

Column 10, line 66, Claim 12, "to the primer by action of the polymerase;" should read --to the primer by action of the polymerase, wherein the dye-labeled dNTP or NTP is labeled with a dye thereby permitting the incorporation of a sequential dNTP or NTP to the 3' end of the dye-labeled dNTP or NTP and wherein said solution consists of a droplet in which an aqueous solution containing said dye-labeled dNTP or NTP, is entrapped within a hydrophobic solvent and the hydrophobic solvent flows through the capillary;--.

Column 11, lines 11-12, Delete Claim 13 in its entirety.

SEQUENCE LISTING

```
<160> NUMBER OF SEQ ID NOS: 4

<210> SEQ ID NO 1
<211> LENGTH: 37
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
ctgctcatat atataggt gccagtcgga tagtgtt                         37

<210> SEQ ID NO 2
<211> LENGTH: 30
<212> TYPE: DNA
<213> ORGANISM: ARTIFICIAL SEQUENCE
<220> FEATURE:
```

-continued

```
<223> OTHER INFORMATION: SYNTHETIC DNA

<400> SEQUENCE: 2
gcggaggaag gtccttggtc attaggatcc                                    30

<210> SEQ ID NO 3
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
aacactatcc gactggcacc                                               20

<210> SEQ ID NO 4
<211> LENGTH: 18
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
ggatcctaat gaccaagg                                                 18
```